(12) United States Patent
Reaux

(10) Patent No.: US 6,827,212 B2
(45) Date of Patent: Dec. 7, 2004

(54) SURGICAL OR MEDICAL INSTRUMENT HOLDER

(76) Inventor: Brian K. Reaux, 710 Rock Hill Dr., Red Oak, TX (US) 75154

( * ) Notice: Subject to any disclaimer, the term of this patent is extended or adjusted under 35 U.S.C. 154(b) by 0 days.

(21) Appl. No.: 10/349,271

(22) Filed: Jan. 22, 2003

(65) Prior Publication Data

US 2003/0196922 A1 Oct. 23, 2003

Related U.S. Application Data

(60) Provisional application No. 60/374,525, filed on Apr. 22, 2002, and provisional application No. 60/383,507, filed on May 26, 2002.

(51) Int. Cl.$^7$ .............................................. B65D 85/28
(52) U.S. Cl. ...................................... 206/372; 206/523
(58) Field of Search ................................ 206/361, 362, 206/362.1, 362.2, 349, 354, 372, 373, 376, 209, 570, 571, 576, 228, 363, 364, 523, 366, 210, 207, 63.3; 211/60.1, 69.1, 70.6, 65; 220/524

(56) References Cited

U.S. PATENT DOCUMENTS

| | | | | |
|---|---|---|---|---|
| 1,471,712 A | * | 10/1923 | Sohnle | 206/361 |
| 2,278,650 A | * | 4/1942 | Drinkwater | 206/361 |
| 2,287,425 A | * | 6/1942 | Fox | 206/523 |
| 2,533,355 A | * | 12/1950 | Comfort | 206/361 |
| 2,945,251 A | * | 7/1960 | Eichner | 206/209 |
| 4,008,808 A | * | 2/1977 | Ramsay | 206/354 |
| 4,013,109 A | | 3/1977 | Sandel | |
| 4,318,473 A | | 3/1982 | Sandel | |
| 4,412,616 A | * | 11/1983 | Williams | 220/524 |
| 4,903,390 A | | 2/1990 | Vidal et al. | |
| 5,024,326 A | * | 6/1991 | Sandel et al. | 206/366 |
| D321,788 S | * | 11/1991 | Chen | D3/74 |
| 5,230,424 A | * | 7/1993 | Alpern et al. | 206/63.3 |
| 5,450,962 A | * | 9/1995 | Uitz | 206/511 |
| 5,533,618 A | * | 7/1996 | Pickels, Jr. | 206/363 |
| 5,566,842 A | * | 10/1996 | Dennis | 211/87 |
| 5,894,921 A | * | 4/1999 | Le et al. | 206/63.3 |
| 6,012,576 A | * | 1/2000 | Onodera | 206/361 |

OTHER PUBLICATIONS

Web pages from http://www.cdc.gov/niosh/sharps2.html—Selecting, Evaluating, and Using Sharps Disposal Containers—I. Introduction, pp. 1–2, Apr. 22, 2002.

Web pages from http://www.cdc.go/niosh/sharps3.html—Selecting, Evaluating, and Using Sharps Disposal Containers—II. Sharps Disposal Containers, pp. 1–7, Apr. 22, 2002.

* cited by examiner

Primary Examiner—Shian T. Luong
(74) Attorney, Agent, or Firm—Grady K. Bergen

(57) ABSTRACT

A device for holding scalpels or other instruments is provided. The device includes a non-fixed sterile body having at least one instrument mounting station that includes a holding portion for releasably holding the proximal end of a surgical or medical instrument while allowing access to the proximal end for grasping and removal of the instrument from the device by a user. The device has a recessed area for receiving the distal end of the instrument to facilitate preventing of inadvertent contact of the distal end by the user while the instrument is held by the device.

9 Claims, 5 Drawing Sheets

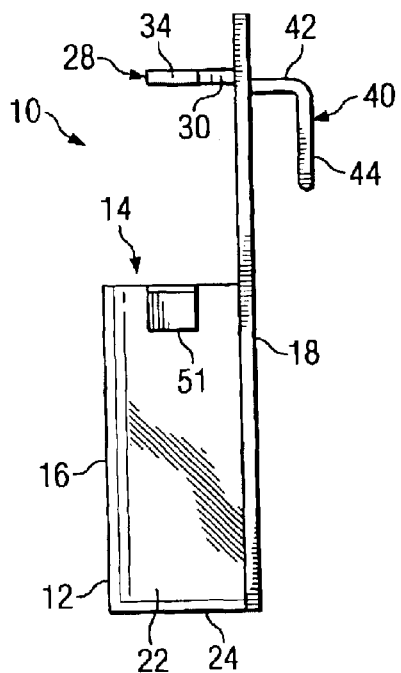
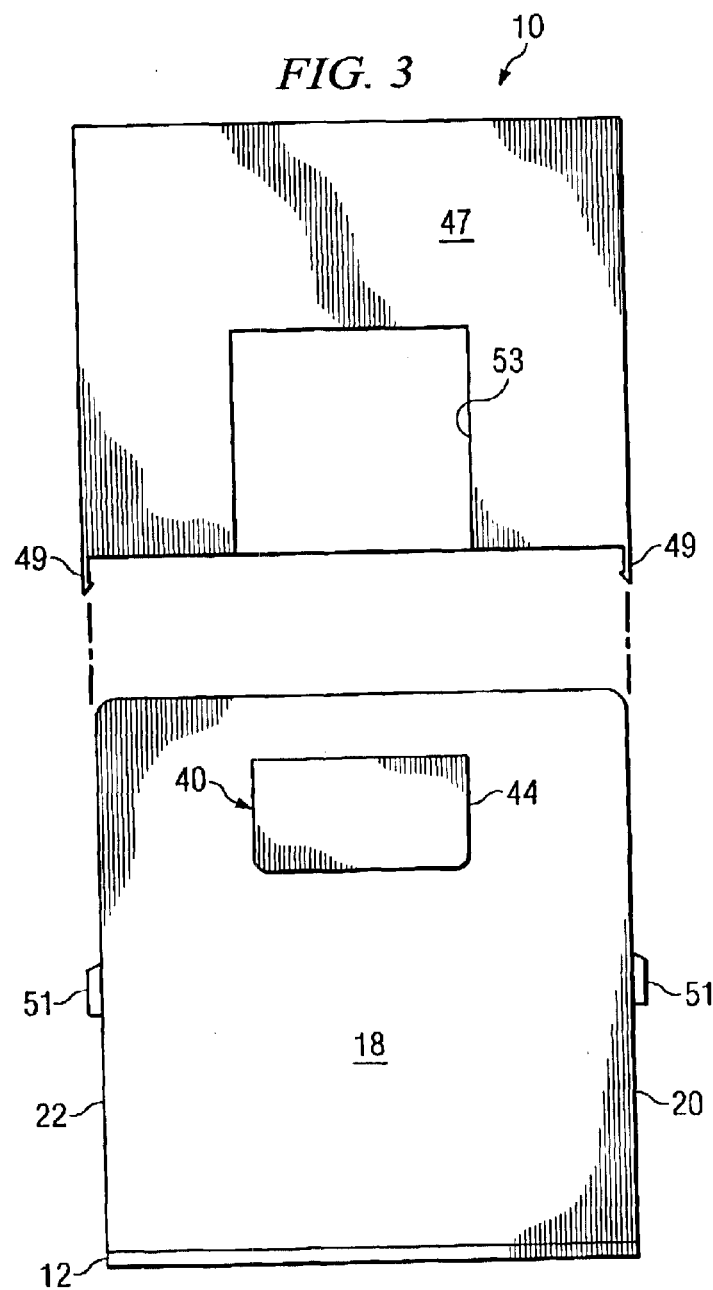

SURGICAL OR MEDICAL INSTRUMENT HOLDER

This application claims the benefit of U.S. Provisional Patent Application Nos. 60/374,525, filed Apr. 22, 2002 and 60/383,507, filed May 26, 2002.

BACKGROUND

This invention relates to surgical or medical equipment.

BRIEF DESCRIPTION OF THE DRAWINGS

For a more complete understanding of the present invention, and the advantages thereof, reference is now made to the following descriptions taken in conjunction with the accompanying figures, in which:

FIG. 2 is an elevational side view of the lower portion of the device of FIG. 1;

FIG. 3 is a rear elevational view of the device of FIG. 1;

DETAILED DESCRIPTION

Figure 1:
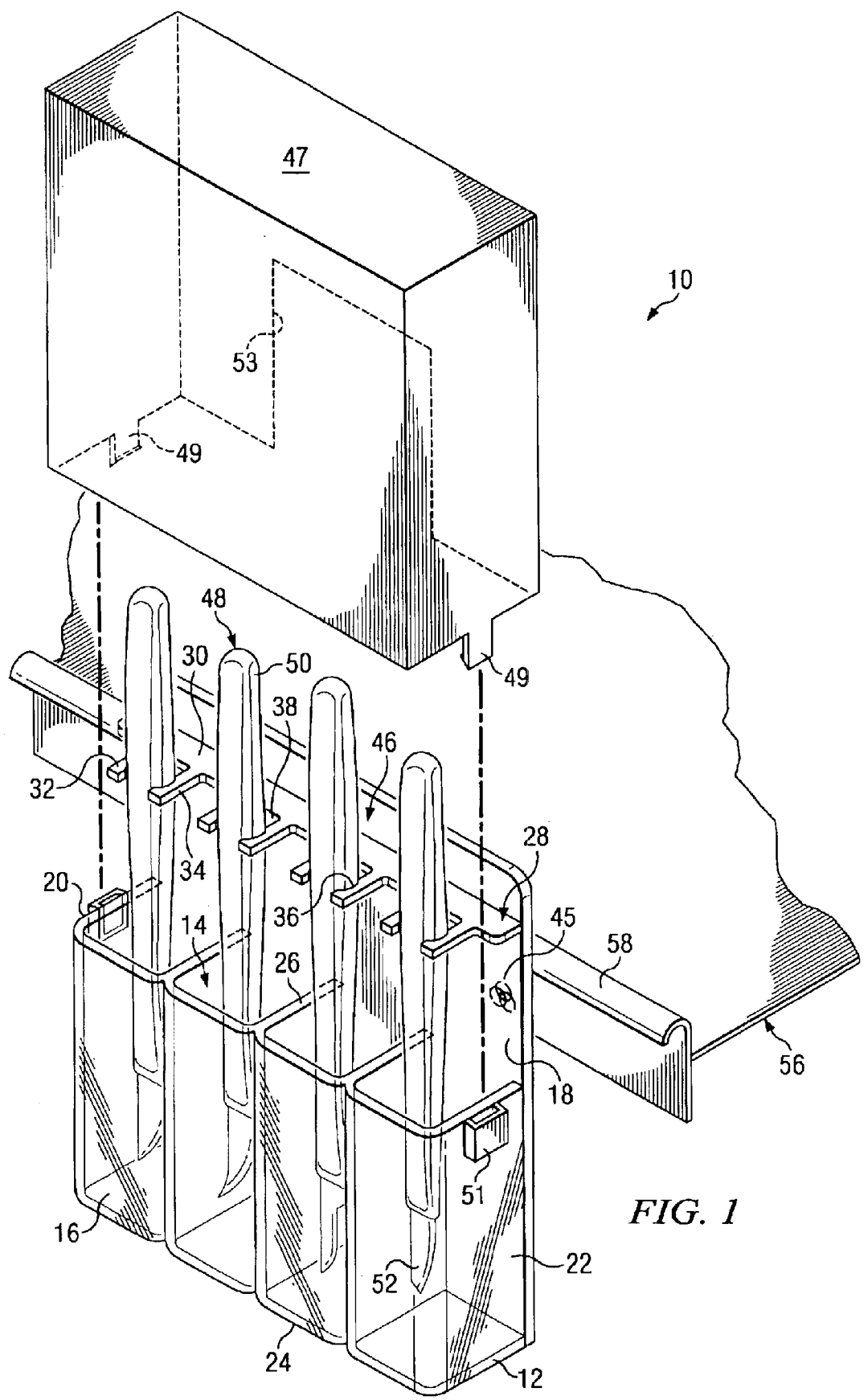
FIG. 1 is a front perspective view of a device for holding scalpels or other instruments.

Referring to FIG. 1, a surgical or medical instrument non-fixed holding device 10 is shown. As used herein, the expression "non-fixed" is to be construed to mean that the device is not permanently attached, fixed or mounted to any furniture, equipment or other support structures that may be provided in surgical or medical environments or is not attached, fixed or mounted for such extended periods such that the sterile integrity the device would become compromised. The device 10 can be used for holding surgical scalpels, but may be used for other devices. As used herein, the expression "surgical" or "medical instruments," may also be construed to include those used in similar non-surgical or non-medical applications, such as dental or therapeutic instruments, that may be used in a sterile environment or where the sterility of the instrument and its environment are important. For purposes of description, reference may be made to a surgical scalpel or scalpels, however, it should be apparent to those skilled in the art at other surgical or medical instruments could be substituted.

The device 10 may include a base 12 having a plurality of recessed areas 14 that form compartments for receiving a distal end of a scalpel or other instrument. The recessed areas 14 are defined by an upright front wall 16 and a rear wall 18 of the device 10, which extends upward from the base 12, as shown. As used herein, "upright" and other expressions that may be used to describe relative orientation may be used solely for convenience. It should be apparent to those skilled in the art, that different orientations may be used or achieved. Therefore such terms should not be construed in a limiting sense. Opposite upright sidewalls 20, 22 extend between the front and rear walls 16, 18. A bottom wall or floor 24 may be provided to close off the lower end of the compartments 14. A layer of foam or other material (not shown) may be provided in the bottom of each recessed area 14, overlaying the wall 24.

Partition walls 26 interposed between the sidewalls 20, 22 at various distances, and extending between the front and rear walls 16, 18, define and separate the individual compartments or recessed areas 14. All or a portion of the material that defines the recessed areas 14 may be transparent or substantially transparent to allow visual perception into the interior of these areas.

The upright rear wall 18 extends upward a distance beyond the upper extent of the compartments 14. Provided on the rear wall 18 is a scalpel or instrument holding portion 28 positioned above the compartments 14. As shown, the holding portion 28 includes a forward projecting member 30 that extends across the width of the wall 18.

A plurality of retainer arms 32, 34 project forward from the member 30. The retainer arms 32, 34 correspond to one another in pairs and may be indented, grooved, slotted, such as at the area 36, or otherwise configured, contoured, textured, etc., on their inner surface, for receiving and to facilitate the holding of the handle or proximal end of a scalpel or other instrument. The arm pairs 32, 34 are each positioned above one of the compartments 14. The combination of the arm pairs 32, 34 and corresponding compartment 14 forms a mounting station for a scalpel or other instrument. In the embodiment shown, four mounting stations are provided for holding four scalpels or instruments. It should be apparent, however, that any number of mounting stations could be provided with the device. The arms 32, 34 may be formed from a material that has sufficient elasticity or resiliency so that corresponding arms 32, 34 can be spread apart or deformed during insertion and removal of the instrument laterally through the forward opening or gap 38, between the arms 32, 34. Optionally, the arms 32, 34 may be spaced apart a distance so that insertion of the instrument through the gap 38 causes the arms 32, 34 to be spread apart or otherwise deformed such that the elasticity of the arms 32, 34 causes an inward biasing force that frictionally holds the scalpel in place between the arms, with the distal end of the scalpel being suspended above the surface of the bottom wall 24.

In an alternate embodiment or method of use, the projecting arms 32, 34 may be used as a longitudinal rest to hold the instrument in place by providing an opening of limited width or dimension, such as the gap 38, wherein the proximal end of the scalpel has at least one transverse dimension that is great enough to prevent further downward longitudinal passage of the instrument through the opening, thus holding or suspending the scalpel or instrument held within. It should be apparent to those skilled in the art, that other structures, such an enclosed aperture, may also be used for such purposes.

In still another alternative embodiment or method of use, the arms 32, 34 or other structure may serve as a transverse rest wherein the surgical or medical instrument is supported by resting on the bottom wall 24, with lateral or transverse movement of the scalpel between the arms 32, 34, or other structure, being limited so that the scalpel is held or retained in a generally upright manner. It may be preferable, however, in many cases to prevent the distal end or blade end of the scalpel or other instrument from resting on the bottom, to prevent dulling or other damage to the scalpel blade. A layer of padding, foam or other protective material (not shown) may be provided in the bottom of each compartment 14 to prevent damage to the instrument or scalpel, should it touch or rest thereon.

In another embodiment, the compartments 14 may be of sufficient depth and configuration such that they achieve the holding function, holding the scalpels or instruments in an upright manner, with the proximal ends or handles of the instruments being presented for grasping. In such an embodiment, the compartments serve as a holding portion so that the arms 32, 34 may be eliminated.

The device 10 may also include a mounting portion 40 for mounting to a support structure, such as a table, stand, or other structure or piece of furniture. As shown in the embodiment of FIG. 2, the mounting portion 40 may be a lip or arm having a rearward projecting member 42 and a downward projecting member 44. These may be configured to engage the rim of a Mayo tray, as shown in FIG. 1, which is commonly employed in surgical or medical environments. Alternate configurations or other means for securing the device to support structures of different configurations and materials may be used as well. These may include, but are not limited to, straps, hooks, brackets, clips, magnets, adhesive, suction devices, or other fasteners that allow the device to be at least temporarily mounted or secured to a support structure. The mounting portion 40 may be configured to provide a secure fit to the support structure to which it is mounted so that the device 10 remains substantially immobile during insertion or removal of scalpels or instruments. The device 10 may be free standing, as well. When free standing, the mounting portion of the device includes the portion of the device that engages the support structure, such as the bottom surface of the wall 24 as it rests on a table or other structure.

The device 10 may be provided with indicia 45 (FIG. 1) to indicate that it may constitute or contain a biohazardous material. All or a portion of the device 10 may be colored (such as the color red to indicate a biohazard) or otherwise provided with indicia or symbols to indicate its nature or use.

A lid or cover 47 may also be provided with the device 10. The cover 47 is sized and configured to fit over the lower portion of the device 10, including any scalpels or instruments 48 held therein so that the instruments 48 are enclosed within the device 10. This is used in situations where the entire device 10, including any instruments held within, are disposed of as a unit. The cover 47 is provided with locking tabs 49 that are received within corresponding slots or receptacles 51 formed on the sidewalls 20, 22. A cutout portion 53 may be provided in the rear wall of the cover 47 (FIG. 3) to accommodate the mounting portion 40.

The device 10 may be sterile or sterilizable. Sterilization may be done through sterilization techniques that are well known in the art, such as chemical, radiation or heat sterilization methods. The device may be manufactured in whole or in part from plastic or polymer materials, glass, fiberglass, paper, cardboard, metal, composite or various other materials that may be subjected to one or more known sterilization methods without significant degradation to the device or that may manufactured in a sterile manner.

In certain embodiments, the device may be disposable or provided as a single-use item. In other embodiments, it may be reusable, with the device being resterilized prior to reuse. The device 10 may be packaged in an openable sealed container or packaging (not shown) to prevent contamination and to maintain sterile integrity of the device during handling and storage prior to use.

In use, the device 10 is removed from any supplied packaging. It may be desirable to use sterile handling procedures so that the sterile integrity of the device 10 is maintained after its removal from any sterile packaging. The device 10 may be filled with selected scalpels or other instruments by inserting each item within one of the mounting stations 46, formed by the retaining arms 32, 34 and compartments 14. The mounting stations 46 also allow accounting of the scalpels or instruments. Numeral, alphabetical or other indicia (not shown) may be provided for each mounting station to facilitate accounting of the instruments held within the device 10.

As shown in FIG. 1, scalpels 48 are inserted with the handle 50 of each scalpel 48 being received between arms 32, 34. The distal end of the scalpel 48 is received within the corresponding compartment 14 beneath so that blade 52 is not exposed, but is located at a position below the upper extent or edge of the compartment 14. Additionally, the scalpel 48 is inserted between the arms 32, 34 in a transverse or crosswise manner so that the profile of the blade 52 faces forward and is readily observable and identifiable to facilitate selection and use. The walls 16, 20, 22 each act as a shield that helps prevent inadvertent contact of the distal end or blade 52 by the user while the instrument is held by the device 10. In the embodiment shown, the scalpel 48 is held within the arms 32, 34 so that the blade 52 is at an elevated position above the compartment floor 24 and a distance apart from the compartment sidewalls to prevent contact and damage to the blade 52. In certain embodiments, the device 10 may be pre-filled or pre-supplied with scalpels or desired instruments already in place within the device.

The device 10 may be positioned on or mounted to a support structure, such as the Mayo tray 56 or IV stand. In the embodiment shown, the mounting portion 40 is positioned over the rim 58 of the tray 56 so that the device 10 is secured thereto. The transparent material forming the walls of the compartment 14 allows one to observe the distal end of the instrument while it is held in the device to facilitate instrument selection. Once the scalpel or instrument is selected, the user may grasp the instrument 48 by the proximal end or handle so that it is released from the arms 32, 34. The instrument 48 is then withdrawn from the compartment 14 for use. After use of the scalpel or instrument 48, it may be returned to and retrieved from the mounting station 46 of the device in a manner similar to that described above.

After use of the device 10, non-disposable scalpels 48, such as used in surgical operating environments, or other non-disposable instruments may be removed from the device 10. The device 10 may then be disposed of. If the scalpels or instruments are disposable, they may be left in the lower portion of the device 10. The cover 47 may then be positioned over the instruments, with the locking tabs 49 being received in the receptacles 51. With the cover 47 in place, the entire device with the instruments contained therein may be disposed of in a suitable manner, such as may be used for disposing of biohazardous waste materials, if necessary. The locking tabs 49 and receptacles 51 can be configured so that the cover 47 is non-releasable and remains permanently locked to the lower portion of the device 10.

Alternatively, if constructed for reuse, the device 10 may be resterilized using known sterilization techniques.

Non-limiting examples of other instruments, in addition to scalpels, that may be held by the device include dental picks or other dental instruments, scalpel blade counters, needle counters, skin markers, cautery pencils, electrosurgical pencils, syringes, suture needle counters, and scalpel blade removers.

Figure 4:
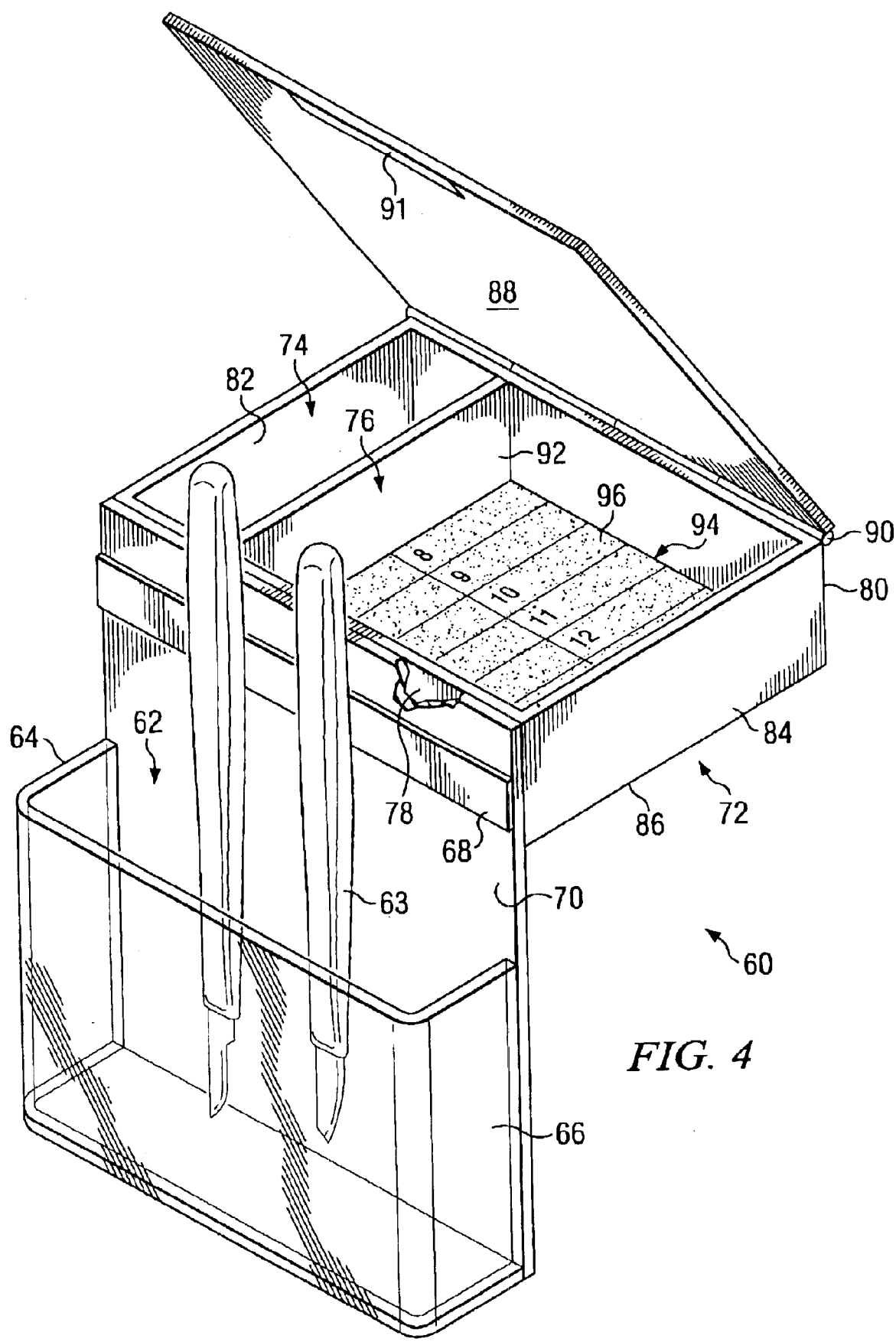
FIG. 4 is a front perspective view of another embodiment of a device for holding scalpels or other instruments.
Figure 5:
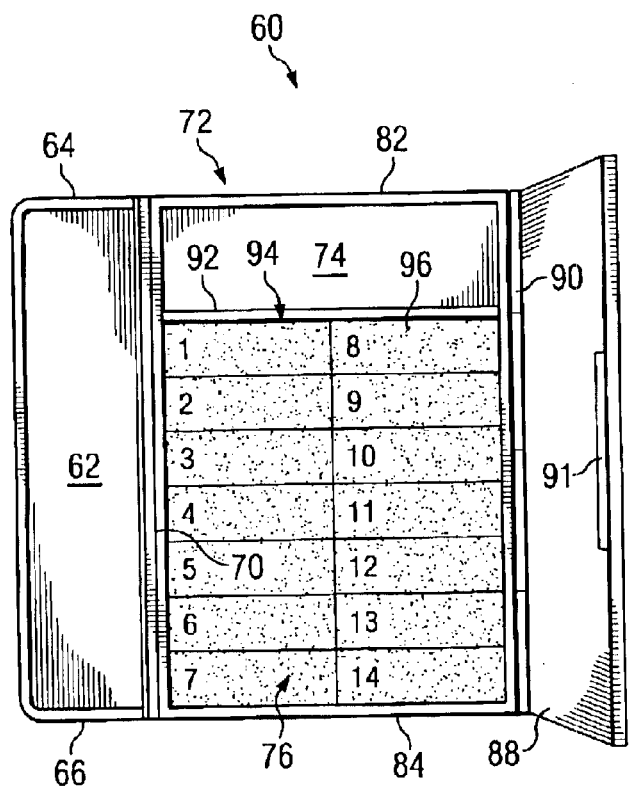
FIG. 5 is a top plan view of the device of FIG. 3.
Figure 6:
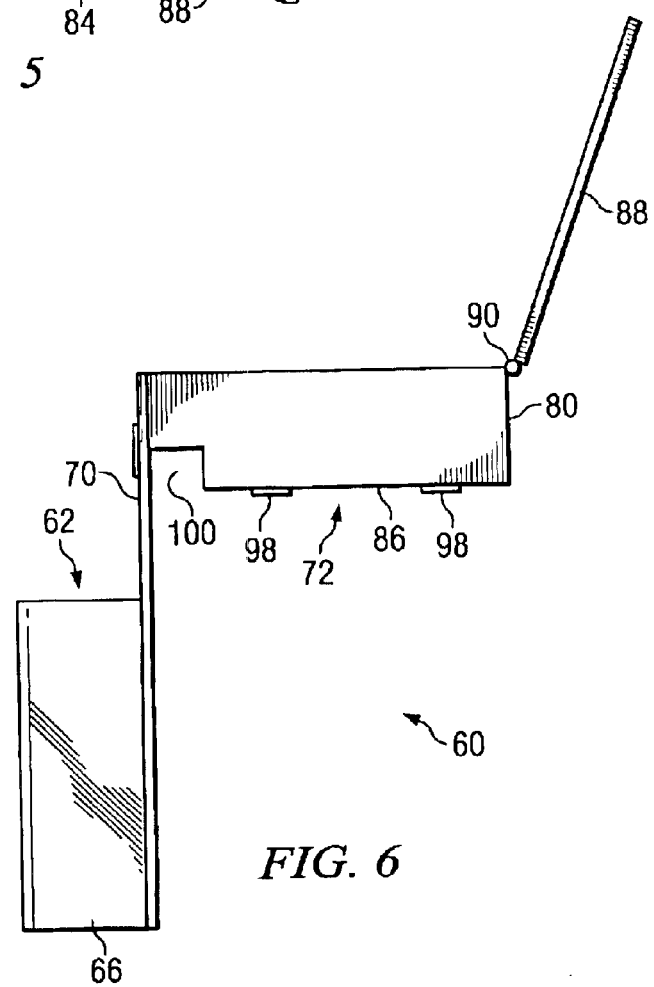
FIG. 6 is an elevational side view of the device of FIG. 3.

In another embodiment of the invention shown in FIGS. 4–6, a holding device 60 is provided that is similar to the device 10. The device 60 may be provided as a sterile device that is disposable after use. The device 60 differs from the device 10 in some respects, however, as is described below. A single compartment or recessed area 62 without internal partitions is provided for receiving the blades or distal ends of the scalpels or instruments 63 instead of individual compartments. Endwalls 64, 66 are provided at the ends of compartment 62.

The holding portion 68 may utilize an attracting or holding member, which may be in the form of a strip, layer or other portion located along the upper portion of the rear wall 70 for holding scalpels or instruments in place. At least one of the member 68 or scalpel or instruments 63 may be of a ferromagnetic material or have components formed from such materials. The other of the member 68 or instrument 63 may be formed from or have components formed from a material that is magnetically attracted to such ferromagnetic material so that the scalpel or instrument is held or retained in a generally upright position. An adhesive or other material having attracting or adhering properties may also be substituted for the magnetic material in certain embodiments. Additionally, a complementary hook and loop fastener material, such as Velcro® fastener material, may be provided as the member 68 and as a component of the instrument 63.

An instrument disposal portion 72 is provided with the device 60. The disposal portion 72 includes a scalpel blade disposal compartment 74 and a suture needle holding compartment 76. The disposal portion 72 is joined along one edge or side wall 78 to the rearward side of the rear wall 70, generally at its upper extent. The disposal portion 72 is defined by the forward sidewall 78, an opposite rear wall 80, end walls 82, 84, which extend between the walls 78, 80, and a bottom wall or floor 86. A lid or cover 88 may also be provided with the disposal portion 72 to cover one or both of the compartments 74, 76. In the embodiment shown, the lid 88 is joined to the rear wall 70 by a hinge 90, so that the lid 88 may be selectively opened or closed. A closure or fastening mechanism 91 is also provided to fasten the lid 88 in place to close and cover the compartments 74, 76. The closure 91 may be non-releasable, so that once the lid 88 is closed it can no longer be opened.

An internal partition 92 divides the compartments 74, 76. The suture needle holding compartment 76 is provided with a layer of foam, cardboard, fabric or other enclosing material 94 into which a suture needle may be inserted and held there by the material 94. The surface of the foam or layer 94 may be provided with visible indicia, such as numerals, letters, borders, etc., to assist in identification of individual suture stations, such as the suture station 96. The numeral or letter indicia may be sequential. The indicia on the separate suture stations facilitate accounting of sutures.

The scalpel blade compartment 74 is separate from the suture compartment 76. Although not shown, a scalpel blade removal device or mechanism may be incorporated with the compartment 76 or disposal portion 72. Such devices or mechanisms are known in the art, such as disclosed in U.S. Pat. Nos. 4,318,473 and 4,903,390.

Referring to FIG. 6, the outer surface of the bottom wall 86 may include a mounting portion 98, which in the embodiment shown may be an adhesive material, hook and loop fastener material, magnetic material, suction fastener or other fastening material or mechanism for temporarily mounting the device 60 to a support structure, such as the surface of a Mayo tray. The support structure may be provided with a complimentary fastening material or mechanism, if necessary. In the embodiment shown, a recessed area 100 is provided to accommodate the lip or rim of a Mayo tray. The device 60 may be configured differently to accommodate other support structures of differing configurations.

In use, the device 60 is used for holding scalpels or instruments 63 in a manner similar to that described with reference to the device 10, with the distal ends of the instruments 63 being received in the compartment 62 and the handles or proximal ends of the instruments being held by the holding portion 68.

After use of scalpels, the used scalpel blades may be placed in the compartment 74. The compartment 74 may also be sized to receive the entire scalpel, where disposable scalpels are employed. Other contaminated or hazardous instruments or instrument components may be placed in the compartment 74, such as used syringes or syringe needles.

Used suture needles may be discarded and accounted for by inserting each one into a suture station 96.

After use of the device 60, any instruments 63 temporarily held by the device may be removed from their mounting stations. Used scalpel blades, suture needles or other instruments or components that are to be discarded are placed in the appropriate compartment 74, 76 and the lid 88 is shut to enclose the objects contained within the compartments 74, 76. The device 60 and its contents may then be discarded in a suitable manner.

Figure 7:
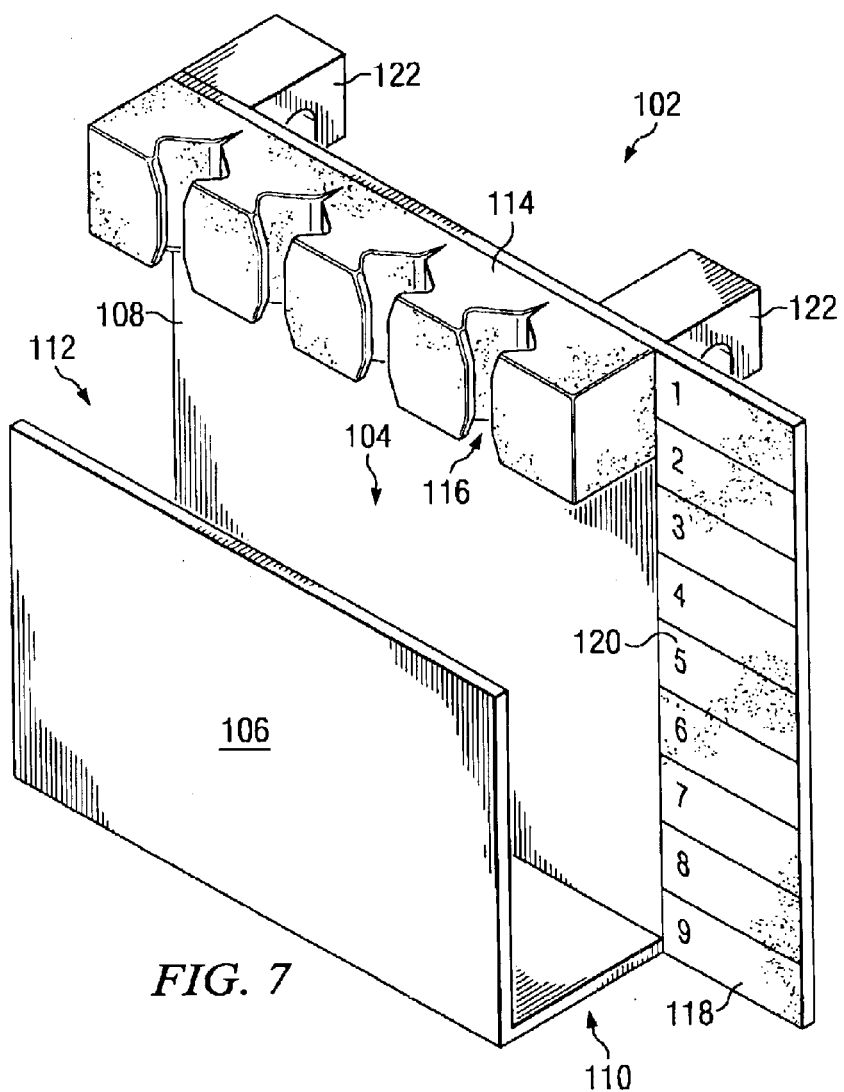
FIG. 7 is a front perspective view of still another embodiment of a device for holding scalpels or other instruments.
Figure 8:
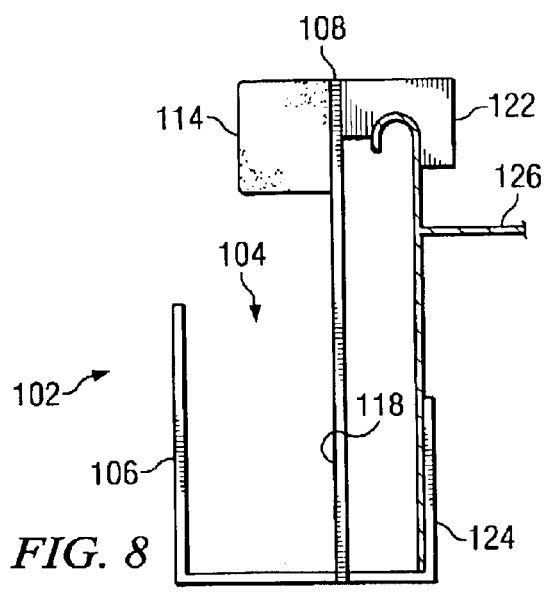
FIG. 8 is an elevational side view of the device of FIG. 7.

Referring to FIGS. 7 and 8, another embodiment is shown. The device 102 is similar to the devices 10 and 60. The device includes a recessed area or compartment 104 defined by forward and rear walls 106, 108, respectively, for receiving the distal ends of scalpels or other instruments. The ends 110, 112 of the compartment are open, however. An instrument holding portion 114 is provided from a compressible or deformable foam material joined generally along the upper portion of the rear wall 108. The foam material 114 is provided with spaced apart slots 116 for receiving scalpels or other instruments.

A suture holding portion 118 is provided and is joined to and coextends along one edge to a side edge of rear wall 108. The suture holding portion 118 is provided with indicia 120 to provide visibly distinguishable suture stations.

A mounting portion is provided and is formed by upper arms 122 and lower arms 124 (FIG. 8) for mounting to the perimeter 126 of a Mayo tray.

In use, scalpels or other instruments are held by the device 102, which may be sterile, within the slots by the compressed foam material of the holding portion 114. Used suture needles may be inserted into the various stations 120 of the suture portion 118. The device 102 may be disposable as well.

The invention provides a device for conveniently holding scalpels or other instruments in a position where they are readily available for use. The device is hands-free and self-serving so that there is no need for handling of the device or passing of instruments, which can lead to inadvertent or accidental sticks or cuts. The scalpels or instruments are provided in a way that only the surgeon or doctor need handle the scalpels or instruments, thus eliminating passing that can increase the risk of sticks or cuts. The device is non-fixed so that it can be positioned or mounted only when needed, so that it never comes into patient contact. The instruments are held so that they can be readily observed for selection and can be easily removed and replaced with one hand. Further, the device may be a disposable unit and can be provided with means for disposing of instruments held within the device or in a separate disposal compartment of the device without danger of instruments held within causing danger to those handling such disposed waste.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

I claim:

1. A disposable device for holding surgical or medical instruments having a proximal end and a distal end, the device comprising a non-fixed sterile body having a plurality of instrument mounting stations that are spaced apart from each other, each mounting station including a holding portion that includes at least one of a rest, a frictional holder, a magnetic holder, a hook and loop fastener holder, and an adhesive holder for releasably holding the proximal end of a medical instrument while allowing access to the proximal end for grasping and removal of the instrument from the device by a user and having a recessed area for receiving the distal end of the instrument to facilitate preventing of inadvertent contact of the distal end by the user while the instrument is held by the device, the body having a suture needle holding portion having at least one suture station having an enclosing material wherein a suture needle of a suture may penetrate and be held by the enclosing material, and further including an instrument disposal portion having a receiving area for receiving and storing used surgical or medical instruments, and wherein the instrument disposal portion is provided with a closure to make the receiving area inaccessible.

2. The device of claim 1, further comprising:

a support structure mounting portion for mounting the device to a support structure.

3. The device of claim 1, wherein:

there are a plurality of visually distinguishable suture stations to facilitate accounting of sutures.

4. The device of claim 1, wherein:

the body is provided with indicia indicative of biohazard materials.

5. The device of claim 1, wherein:

at least a portion of the mounting station is substantially transparent to allow visual perception through said at least a portion.

6. The device of claim 1, wherein:

the holding portion holds the surgical or medical instruments in a suspended position so that the distal end of the surgical or medical instruments does not rest on any support surface.

7. The device of claim 1, wherein:

the surgical or medical instruments include a scalpel.

8. The device of claim 1, wherein:

the holding portion releasably holds the surgical or medical instruments to allow access to the proximal end for manually grasping and removing of the instrument from the device by a user with a single hand.

9. The device of claim 1, wherein:

the holding portion holds the surgical or medical instruments in an orientation to facilitate visual perception of a profile of the distal end for visual identification of the instruments.

* * * * *